US00PP30595P2

(12) United States Plant Patent
Trees

(10) Patent No.: US PP30,595 P2
(45) Date of Patent: Jun. 25, 2019

(54) ***BUDDLEIA* PLANT NAMED 'SRPBUDSAN'**

(50) Latin Name: ***Buddleia* hybrid**
Varietal Denomination: SRPbudsan

(71) Applicant: THE CONARD-PYLE COMPANY, West Grove, PA (US)

(72) Inventor: Scott C. Trees, Arroyo Grande, CA (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/732,465

(22) Filed: Nov. 17, 2017

(51) Int. Cl.
*A01H 5/02* (2018.01)

(52) U.S. Cl.
USPC ..... Plt./242

(58) Field of Classification Search
USPC ..... Plt./242
CPC ... A01H 5/02; A01H 5/00; A01H 5/08; A01H 5/0812; A01H 6/30
See application file for complete search history.

(56) References Cited

U.S. PATENT DOCUMENTS

PP24,016 P3 * 11/2013 Werner ..... Plt./242
PP25,730 P2 7/2015 Trees

OTHER PUBLICATIONS

Issuu 2018 STAR Roses and Plants Catalog, retrieved on Oct. 4, 2018, retrieved from the Internet at https://issuu.com/starrosesandplants/docs/2018_catalog, cover page, pp. 5, 38, 131 (2017). (Year: 2017).*

* cited by examiner

*Primary Examiner* — June Hwu
(74) *Attorney, Agent, or Firm* — Buchanan Ingersoll & Rooney PC

(57) ABSTRACT

A new and distinct variety of *Buddleia* plant, herein referred to by its cultivar name, 'SRPbudsan', is provided which forms on a substantially continuous basis attractive purplish-red colored flowers. Attractive, dark green colored foliage is formed. The growth habit is moderately vigorous and compact-mounded. The new variety is well suited for providing attractive ornamentation in the landscape.

3 Drawing Sheets

Figure 1:
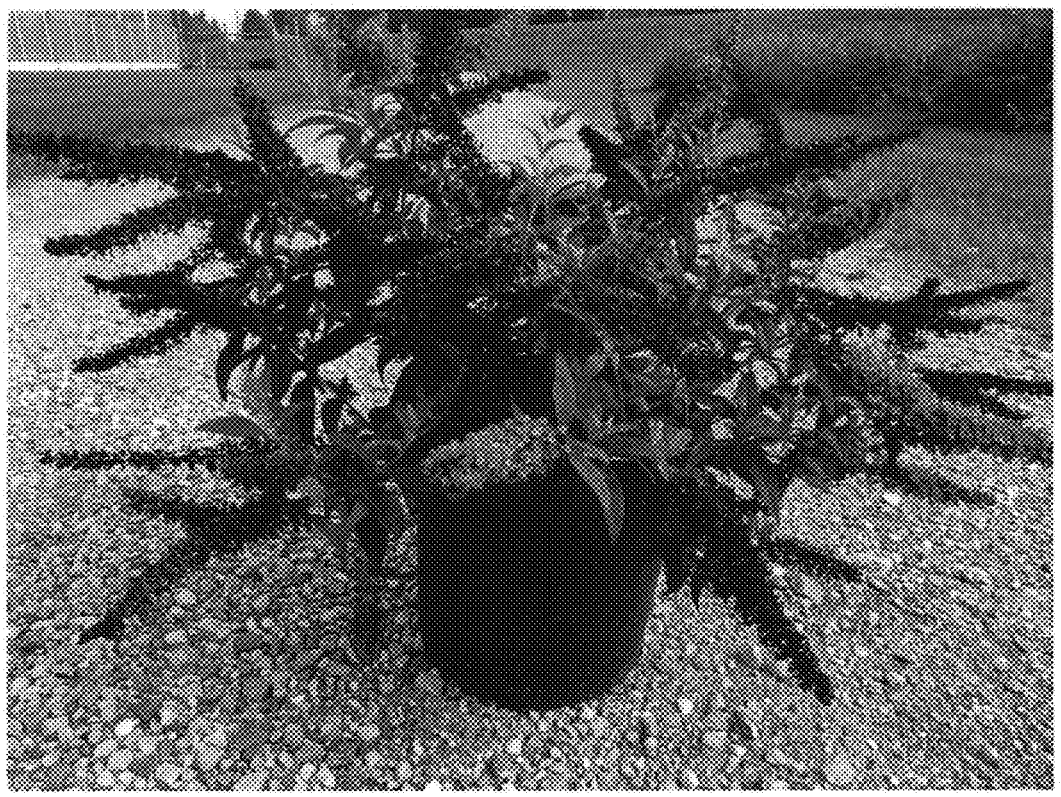

Botanical/commercial classification:
Latin name—*Buddleia* hybrid.
Common name—Butterfly bush.
Varietal denomination: 'SRPbudsan'.

SUMMARY OF THE INVENTION

The new variety of *Buddleia* hybrid plant originated in a controlled breeding program in Guadalupe, Calif. during May 2013. The objective of the breeding program was the development of a series of *Buddleia* cultivars with uniform habits and flower timing, sterility, and repeat flowering. The new cultivar was created by cross-pollination wherein two parents were crossed which previously had been studied in the hope that they would contribute the desired characteristics. The female parent (i.e., the seed parent) was the *Buddleia* hybrid 'Lilac Chip' variety (U.S. Plant Pat. No. 24,016). The male parent (i.e, the pollen parent) was the *Buddleia davidii* 'Attraction' variety (non-patented in the United States).

The parentage of the new variety can be summarized as follows:

'Lilac Chip' x 'Attraction'

The new cultivar was discovered and selected as a single flowering plant from the progeny resulting from the above pollination during August 2014 in a controlled environment in Guadalupe, Calif. Selective study resulted in the identification of a single plant of the new variety.

It was found that the new variety of *Buddleia* plant of the present invention:

(a) substantially continuous basis forms purplish-red colored flowers,
(b) displays dark green colored foliage,
(c) exhibits a moderately vigorous and compact-mounded growth habit, and
(d) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Lilac Chip' variety displays lavender purple colored flowers, medium green colored foliage, and low vigor, while the new variety provides purplish-red colored flowers, dark green colored foliage, and moderate vigor. The 'Attraction' variety (i.e., the pollen parent) displays lavender purple colored flowers, medium green-colored foliage, and a vigorous and upright growth habit, while the new variety displays purplish-red colored flowers, dark green colored foliage, and a moderately vigorous and compact-mounded growth habit.

The new variety can also be distinguished from other similar varieties that are commercially available. For instance, the new variety of the present invention can readily be distinguished from the 'Boscranz' (U.S. Plant Pat. No.

25,730) variety, as the new cultivar displays a more compact and better mounded growth habit than the 'Boscranz' variety and the flowers of the new variety are more red in color than the flowers of the 'Boscranz' variety.

The new variety has been found to undergo asexual by a number of routes, including terminal stem cuttings. Asexual propagation by the above-mentioned techniques in Guadalupe, Calif. since December 2014 has shown that the characteristics of the new variety are stable and are strictly transmissible by such asexual propagation from one generation to another. Accordingly, the new variety undergoes asexual propagation in a true-to-type manner.

The new variety has been named 'SRPbudsan'.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'SRPbudsan' variety. The plants were grown in three-gallon pots for approximately four months outside at West Grove, Pa. Plants were pinched once after transplant.

FIG. 1—illustrates a specimen of the plant displaying the overall growth and flowering habit—side view.

Figure 2:
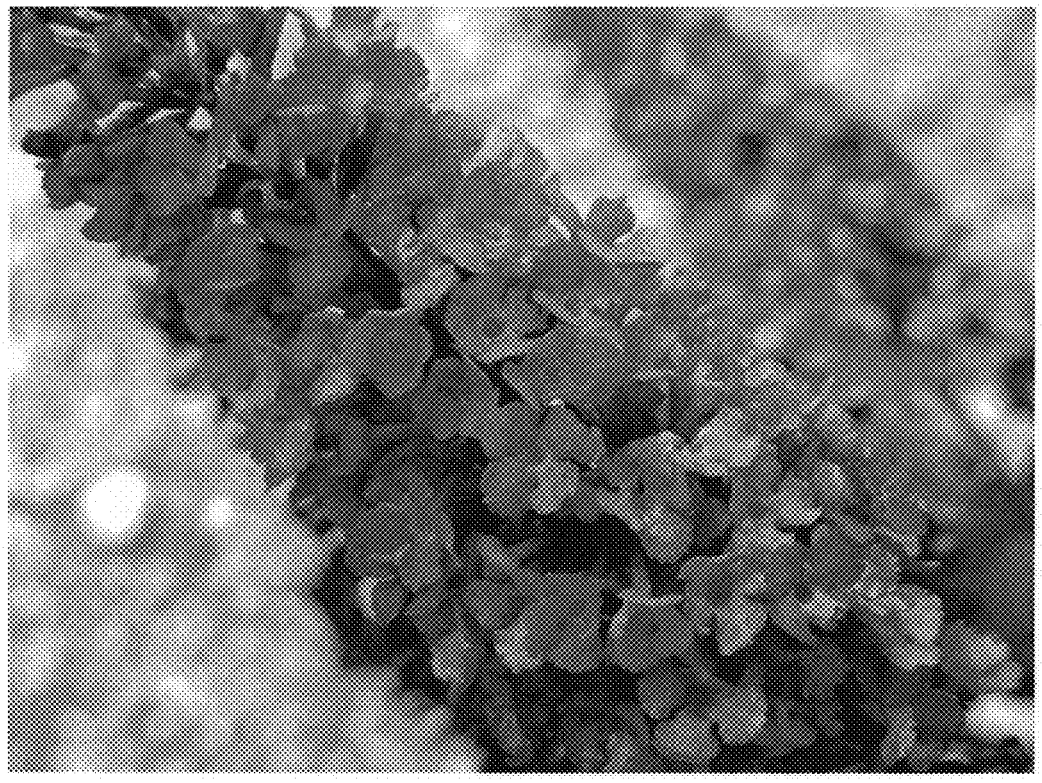

FIG. 2—illustrates a specimen of an inflorescence in the course of opening.

Figure 3:
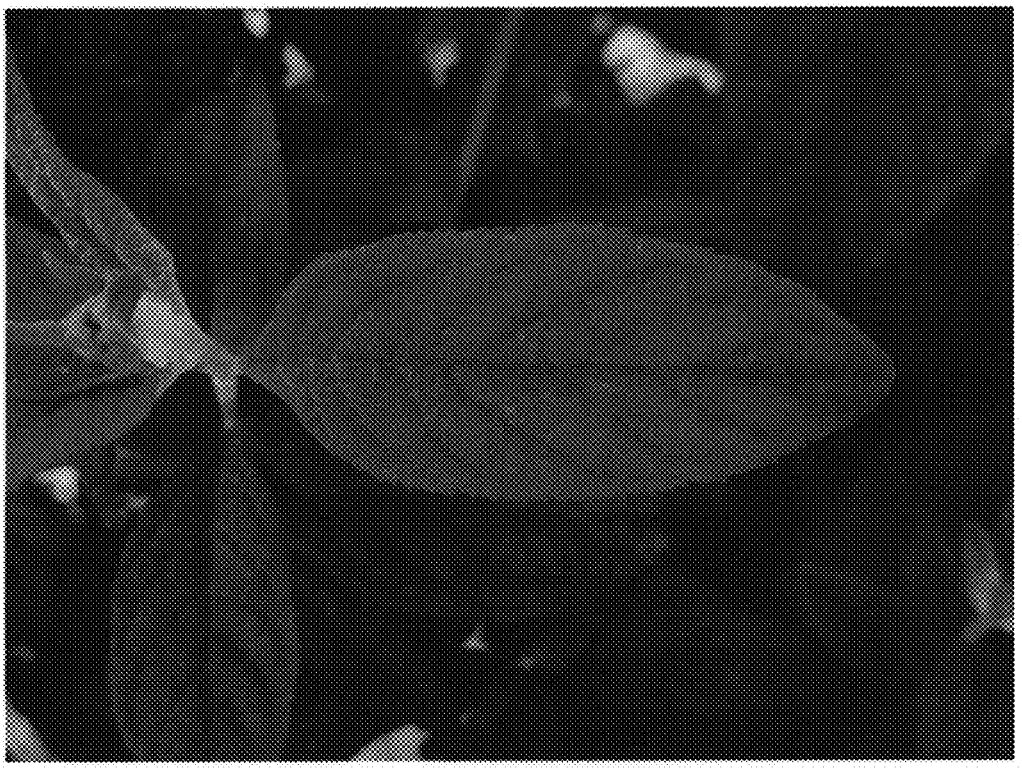

FIG. 3—illustrates a specimen of a leaf—plan view—obverse.

DETAILED BOTANICAL DESCRIPTION

The chart used in the identification of the colors is that of The Royal Horticultural Society (R.H.S. Colour Chart), 2015 edition, London, England. The terminology which precedes reference to the chart has been added to indicate the corresponding color in more common terms. The color values were determined in August 2017 under natural light conditions in West Grove, Pa. The description is based on the observation of plants produced from cuttings from stock plants and grown in three-gallon containers for approximately four months in an outdoor nursery in West Grove, Pa. Plants were pinched once after transplant.

Class: *Buddleia* Plant.

Propagation:

- *Type cutting*.—Terminal stem.
- *Time to initiate roots*.—Approximately 10 to 14 days on average.
- *Time to produce a rooted cutting*.—Approximately 21 to 25 days on average.
- *Root description*.—Fibrous.
- *Rooting habit*.—Freely branching.

Plant:

- *Habit*.—Moderate growth vigor and compact-mounding.
- *Commercial crop time*.—Approximately 2 months from a rooted cutting to finish in a 3 gallon container on average.
- *Size*.—Approximately 40.0 cm in height from soil level to top of plant plane on average; and approximately 62.0 cm in width on average.

Branches:

- *Branching habit*.—Freely branching, pinching enhances basal branching.
- *Quantity of main branches per plant*.—Approximately 6 on average.
- *Strength*.—Commonly strong, somewhat flexible and becomes woody with age.
- *Size*.—Length: approximately 28.0 cm on average. Diameter: approximately 6.0 mm on average. Length of central internode: approximately 4.5 cm on average.
- *Texture*.—Viscid, densely glandular pubescent.
- *Color*.—Young stems: commonly near Yellow-Green Group 145A. Mature stems: commonly near Grey-Brown Group 199A.

Foliage:

- *Number of leaves*.—Approximately 90 per branch on average; and approximately 20 per branched lateral stem on average.
- *Fragrance*.—None detected.
- *Form*.—Simple.
- *Arrangement*.—Opposite.
- *Durability to stress*.—Moderate to high.

Leaves:

- *Aspect*.—Primarily perpendicular to stem.
- *Shape*.—General: lanceolate to oblanceolate. Margin: serrulate. Apex: acute. Base: attenuate.
- *Venation pattern*.—Pinnate, reticulate.
- *Size*.—Length of mature leaf: approximately 11.5 cm on average. Width of mature leaf: approximately 3.7 cm on average.
- *Texture*.—Upper and lower surfaces: smooth, glabrous.
- *Color*.—Upper surface of mature foliage: commonly near between Green Group 137A and 137B. Lower surface of mature foliage: commonly near Yellow-Green Group N148C.
- *Petiole*.—Shape: rounded, slightly curved. Length: approximately 3.0 mm on average. Width: approximately 1.0 mm on average. Texture: densely pubescent with lanulose hairs. Color: commonly near Yellow-Green Group 147B.

Inflorescence:

- *Quantity*.—Approximately 15 open inflorescences per plant on average, and approximately 500 flowers per inflorescence on average, opening from base to apex.
- *Shape*.—Conical.
- *Type*.—Terminal panicles, each panicle having about 2 to 4 branches on average; and flowers persistent, facing upward and outward.
- *Fragrance*.—Very faint.
- *Depth or height*.—Approximately 17.0 cm on average.
- *Width*.—Approximately 3.5 cm on average.
- *Rachis*.—Strength: strong. Length: approximately 17.0 cm on average. Diameter: approximately 2.0 mm on average. Texture: pubescent with stellate hairs. Color: commonly near Yellow-Green Group 146B with pubescence of commonly near Green-White Group 157A.
- *Peduncle*.—Length: approximately 1.0 cm on average. Surface texture: densely pubescent with stellate hairs. Color: commonly near Green Group 137C with pubescence of commonly near White Group NN155C.
- *Density of flowers*.—Dense.

Flower:

- *Type*.—Single, salverform.
- *Bud just before opening*.—Shape: oblong. Length: approximately 6.0 mm on average. Diameter:

approximately 1.0 mm on average. Texture: glabrous. Color of petals: commonly near Red-Purple Group 72A.

*Corolla*.—Shape: rotate, commonly 4 petals arranged in a single whorl. Depth: approximately 1.0 cm on average. Width: approximately 8.0 mm on average. Corolla eye color: commonly near Greyed-Orange Group N163C.

*Petals*.—Shape: rotund. Margin: erosulate. Apex: rounded. Length from throat: approximately 4.0 mm on average. Width: approximately 4.0 mm on average. Texture of upper and lower surfaces: glabrous. Color of upper surface when first and fully open: commonly near Red-Purple Group 72A. Color of lower surface when first and fully open: commonly near Red-Purple Group 72B. Petal attitude when at full flowering: horizontal. Petal arrangement: touching. Incision of the petal: medium incision.

*Corolla tube*.—Length: approximately 7.0 mm on average. Width: approximately 1.0 mm on average. Diameter of throat opening: approximately 1.0 mm on average. Inner surface: texture is lightly pubescent and coloration is commonly near Orange Group N25C. Outer surface: texture is glabrous and coloration is commonly near Red-Purple Group 68A.

*Calyx*.—Shape: tubular. Length: approximately 3.0 mm on average. Diameter: approximately 1.0 mm on average.

*Sepals*.—Quantity per flower: commonly 4 on average, fused at base. Length: approximately 3.0 mm on average. Width: approximately less than 1.0 mm on average. Apex: acute. Margin of free portion: entire. Inner surface: Texture: glabrous. Color: commonly near Green Group 137A. Outer surface: Texture: moderately pubescent. Color: commonly near Green Group 137B with near Greyed-Purple Group 187A at margins and pubescence of near White Group NN155A.

*Pedicles*.—Strength: strong, flexible. Length: approximately 1.0 mm on average. Width: approximately 1.0 mm on average. Texture: densely pubescent with stellate hairs. Color: commonly near Green Group 137D with pubescence of near White Group NN155A.

*Reproductive organs*.—Androecium: Stamen: commonly 4 per Flower, completely adnate to corolla. Anther: shape is lanceolate, length is approximately 1.0 mm on average, and coloration is commonly near White Group 155A. Pollen: amount is moderate and coloration is commonly near White Group NN155A. Gynoecium: Pistil: commonly 1 per flower, length is approximately 3.5 mm on average. Stigma: shape is cleft, two-parted, length is approximately 1.0 mm on average, and coloration is commonly near Yellow-Green Group 145A. Style: length is approximately 1.0 mm on average and coloration is commonly near Yellow-Green Group 145B, opaque. Ovary: length is approximately 1.5 mm on average and coloration is commonly near Yellow-Green Group 145A. Seed and fruit: none have been observed to date.

Development:

*Plant hardiness zone*.—Commonly hardy to USDA zone 6.

*Blooming*.—Freely flowering under outdoor growing conditions with substantially continuous blooming from late spring through mid-fall.

*Lastingness of individual flower*.—Approximately 5 days on average.

*Tolerance to disease*.—Not observed to date.

The new 'SRPbudsan' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Buddleia* plant characterized by the following combination of characteristics:

(a) forms purplish-red colored flowers on a substantially continuous basis, (b) displays dark green colored foliage, (c) exhibits a moderately vigorous and compact-mounded growth habit, and (d) is well suited for providing attractive ornamentation; substantially as herein shown and described.

* * * * *